US009964530B2

(12) United States Patent
Baldaccini

(10) Patent No.: US 9,964,530 B2
(45) Date of Patent: May 8, 2018

(54) CONFINED SPACE ENTRY STATION

(71) Applicant: Tracy William Baldaccini, Lake Zurich, IL (US)

(72) Inventor: Tracy William Baldaccini, Lake Zurich, IL (US)

( * ) Notice: Subject to any disclaimer, the term of this patent is extended or adjusted under 35 U.S.C. 154(b) by 257 days.

(21) Appl. No.: 15/063,058

(22) Filed: Mar. 7, 2016

(65) Prior Publication Data

US 2017/0254788 A1  Sep. 7, 2017

(51) Int. Cl.
*G01N 33/00* (2006.01)

(52) U.S. Cl.
CPC ................................ *G01N 33/0062* (2013.01)

(58) Field of Classification Search
CPC .................................................... G01N 33/062
See application file for complete search history.

(56) References Cited

U.S. PATENT DOCUMENTS

| | | | |
|---|---|---|---|
| 3,610,048 A | 10/1971 | Weeks | |
| 3,830,480 A | 8/1974 | Grant | |
| 3,922,921 A | 12/1975 | Woo | |
| 4,279,142 A * | 7/1981 | McIntyre | G01N 33/0006 73/1.06 |
| 4,302,772 A * | 11/1981 | Gillot | G21C 17/08 348/82 |
| 4,415,066 A | 11/1983 | Mensik | |
| 4,761,823 A | 8/1988 | Fier | |
| 4,841,787 A * | 6/1989 | Waterman | G01F 1/40 374/E1.02 |
| 4,858,798 A | 8/1989 | Siddoway et al. | |
| 5,109,718 A | 5/1992 | Gugel et al. | |
| 5,118,462 A * | 6/1992 | Dirauf | B25J 5/02 165/11.2 |
| 5,146,796 A | 9/1992 | Mailliet et al. | |
| 5,295,557 A | 3/1994 | Taylor | |
| 5,481,930 A | 1/1996 | Kuo et al. | |
| 5,632,458 A | 5/1997 | Tollerud | |
| 5,718,104 A | 2/1998 | Kennedy | |
| 5,756,908 A | 5/1998 | Knollmeyer et al. | |
| 6,131,473 A * | 10/2000 | Hoffman | G01N 17/046 73/29.01 |
| 6,148,681 A * | 11/2000 | Gravel | G01F 23/268 73/866.5 |
| 6,234,006 B1 | 5/2001 | Sunshine et al. | |
| 6,282,943 B1 | 9/2001 | Sanders et al. | |

(Continued)

*Primary Examiner* — David Bolduc
(74) *Attorney, Agent, or Firm* — Erickson Law Group, PC

(57) ABSTRACT

A confined space entry station is disclosed. The station has a back plate, an accessory holder, and a probe holding arm. The back plate is configured to attach to a manway of a confined space. The accessory holder is connected to the back plate. The probe holding arm has a connecting segment and a probe holding segment. The probe holding arm has a deployed position and a stored position. The connecting segment is connected to the probe holding segment. The probe holding segment is transverse to the connecting segment. The connecting segment is pivotally connected to the back plate and extends beyond the back plate when the probe holding arm is in the deployed position. The probe holding segment has a surface for supporting a probe. The probe holding segment extends transverse to the back plate when the probe holding arm is in the deployed position.

20 Claims, 5 Drawing Sheets

(56) References Cited

U.S. PATENT DOCUMENTS

| | | | |
|---|---|---|---|
| 6,345,853 B1 | 2/2002 | Price, Jr. et al. | |
| 6,435,046 B1 | 8/2002 | Beaver | |
| 7,172,164 B2 | 2/2007 | Fuelling et al. | |
| 7,253,413 B2 * | 8/2007 | Sauer | G01N 21/3504 250/339.08 |
| 7,261,212 B2 | 8/2007 | Sholem | |
| 7,903,140 B2 | 3/2011 | Metala et al. | |
| 8,109,160 B2 * | 2/2012 | Bossi | G01N 29/225 73/584 |
| 8,286,512 B1 * | 10/2012 | Selbig | G01N 1/16 73/863.41 |
| 8,684,061 B2 | 4/2014 | Porter | |
| 8,935,965 B1 * | 1/2015 | Selbig | G01N 1/16 73/863.41 |
| 9,316,512 B2 * | 4/2016 | Georgeson | G01D 11/30 |
| 9,612,195 B1 * | 4/2017 | Friedman | G01N 21/3504 |
| 9,625,286 B2 * | 4/2017 | Stanton | G01D 11/30 |
| 2003/0101666 A1 | 6/2003 | Veenstra | |
| 2004/0084593 A1 | 5/2004 | Barfield | |
| 2004/0145485 A1 | 7/2004 | Tice | |
| 2005/0098461 A1 | 5/2005 | Kao | |
| 2007/0023371 A1 | 2/2007 | Noga et al. | |
| 2008/0169739 A1 | 7/2008 | Goldenberg | |
| 2009/0278924 A1 * | 11/2009 | Heyworth | F01D 21/003 348/82 |
| 2011/0089937 A1 * | 4/2011 | Petrosky | G01N 27/90 324/220 |
| 2011/0260721 A1 * | 10/2011 | Fischer | G01B 7/105 324/229 |
| 2012/0297868 A1 * | 11/2012 | Elkins | B09B 1/00 73/152.31 |
| 2014/0284222 A1 * | 9/2014 | Wanek, Jr. | G01N 33/0065 205/780.5 |

* cited by examiner

CONFINED SPACE ENTRY STATION

FIELD OF THE INVENTION

This invention relates in general to confined space entry stations.

BACKGROUND OF THE INVENTION

Tanks, vessels, trenches, dikes, and other confined spaces often provide a manway or manhole for allowing a worker to enter the confined space. Some confined spaces contain or previously contained chemicals or other substances.

To ensure worker safety when a worker is working in a confined space, it may be required by law or regulation or it may otherwise be advisable to monitor the air within the confined space for a concentration of one or more elements or compounds that could be injurious to or present a risk to the worker's health. Portable gas monitors have been used to monitor air within confined spaces when workers, such as maintenance personal, are working within the confined space.

However, the present inventor recognized that there is often no suitable or convenient place to place the gas monitor on or adjacent to the manway. Further, the present inventor recognized that manways are often located in industrial or other work areas were the area surrounding the manway is dirty, greasy, watery, or otherwise not suitable for placing sensitive and relatively costly gas monitoring equipment. If the gas monitor equipment is laid in the manway opening, it is an obstacle to ingress and egress through the manway by the worker. Further, the gas monitoring equipment might be damaged or destroyed by a worker during ingress or egress, such as if the gas monitoring equipment is stepped on or knocked off of the manway opening.

The present inventor recognized that even if the gas monitor can be laid in an area surrounding the manway, a probe must extend from the gas monitor outside of the confined space through the manway and into the confined space. The present inventor recognized that when the probe lays on the bottom of the manway opening it is an obstacle ingress and egress through the manway by the worker. The probe can be damaged or destroyed by a worker during ingress or egress. Even if the probe is not damaged during ingress or egress, the probe must be moved or carefully positioned during ingress and egress. Therefore, moving and positioning the probe during ingress and egress adds time and is inconvenient to the worker. Further, if the worker must exit quickly due to an emergency, the probe or the gas monitoring equipment is a potential obstacle to the quick and safe exit of the confined space by the worker.

The present inventor recognized that certain laws, rules, regulations and or best practices require certain documents, such as work permits, to be posted adjacent the manway of a confined space when a worker is working within the confined space. But there is often no convenient place or manner of posting such documents adjacent the manway. The present inventor recognized that certain laws, rules, regulations and or best practices may require an air horn or other audible warning device to be placed adjacent a manway of a confined space when a worker is working within the confined space. But there is often no convenient place or manner of placing the air horn or other sound generating warning device adjacent the manway. The present inventor recognized that certain laws, rules, regulations and or best practices may require a two-way radio or other communication device to be placed adjacent a manway of a confined space when a worker is working within the confined space. But there is often no convenient place or manner of placing the two-way radio or other communication device adjacent the manway. The present inventor recognized the need for a device that will enable the secure placement of several items at or adjacent a manway to a confined space.

SUMMARY OF THE INVENTION

A confined space entry station is disclosed. In some embodiments, the station comprises a back plate, an accessory holder, and a probe holding arm. The back plate is configured to attach to a manway of a confined space. The accessory holder is connected to the back plate.

The probe holding arm comprises a connecting segment and a probe holding segment. The probe holding arm comprises a deployed position and a stored position. The connecting segment is connected to the probe holding segment. The probe holding segment is transverse to the connecting segment. The connecting segment is pivotally connected to the back plate and extends beyond the back plate when the probe holding arm is in the deployed position. The probe holding segment comprises a surface for supporting a probe. The probe holding segment extends transverse to the back plate when the probe holding arm is in the deployed position. In some embodiments, the confined space entry station is a gas monitor mount for a manway.

A method of monitoring a confined space for hazardous gases is also disclosed. In one embodiment, a back plate of a gas monitor mount is connected to a manway at one or more apertures of the manway. A probe holding arm is pivoted about a probe holding arm connection to the back plate to locate the probe holder adjacent to an internal sidewall of the manway in an upper half of a manway opening of the manway. A gas monitor mounted to the back plate is activated to draw air through a tubular probe supported by the probe holding arm extending through the manway.

Numerous other advantages and features of the present invention will become readily apparent from the following detailed description of the invention and the embodiments thereof, from the claims, and from the accompanying drawings.

DETAILED DESCRIPTION

Figure 1:
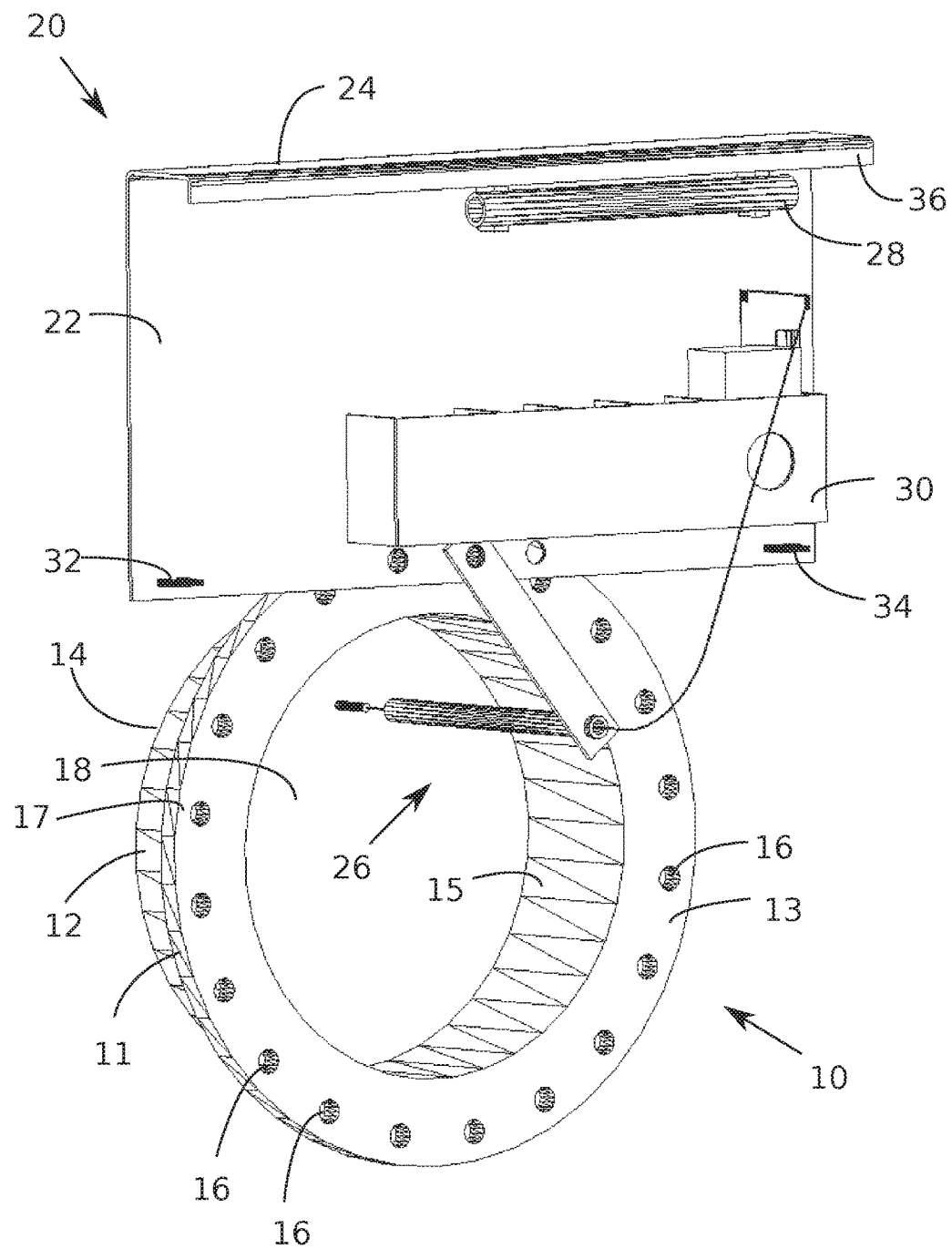
FIG. 1 is a front perspective view of one embodiment of a confined space entry station of the invention mounted to a manway.

The following description is presented to enable any person skilled in the art to make and use the invention. For the purposes of explanation, specific nomenclature is set forth to provide a plural understanding of the present invention. While this invention is susceptible of embodiment in many different forms, there are shown in the drawings, and will be described herein in detail, specific embodiments thereof with the understanding that the present disclosure is to be considered as an exemplification of the principles of the invention and is not intended to limit the invention to the specific embodiments illustrated.

A confined space entry station 20 is disclosed. The station 20 comprises a back plate 22, a top ledge 24, and a probe arm 26. The back plate 22 comprises a probe arm support 28, an accessory holder 30, and an accessory attachment members 32, 34. The top ledge 24 comprises a front lop 36. The top ledge can prevent falling materials, liquid, or debris from contacting the probe arm, accessory holder and other comments under the ledge. The back plate comprises first, second, and third mounting apertures 38, 40, 42 located at a bottom central location on the back plate.

Figure 2:
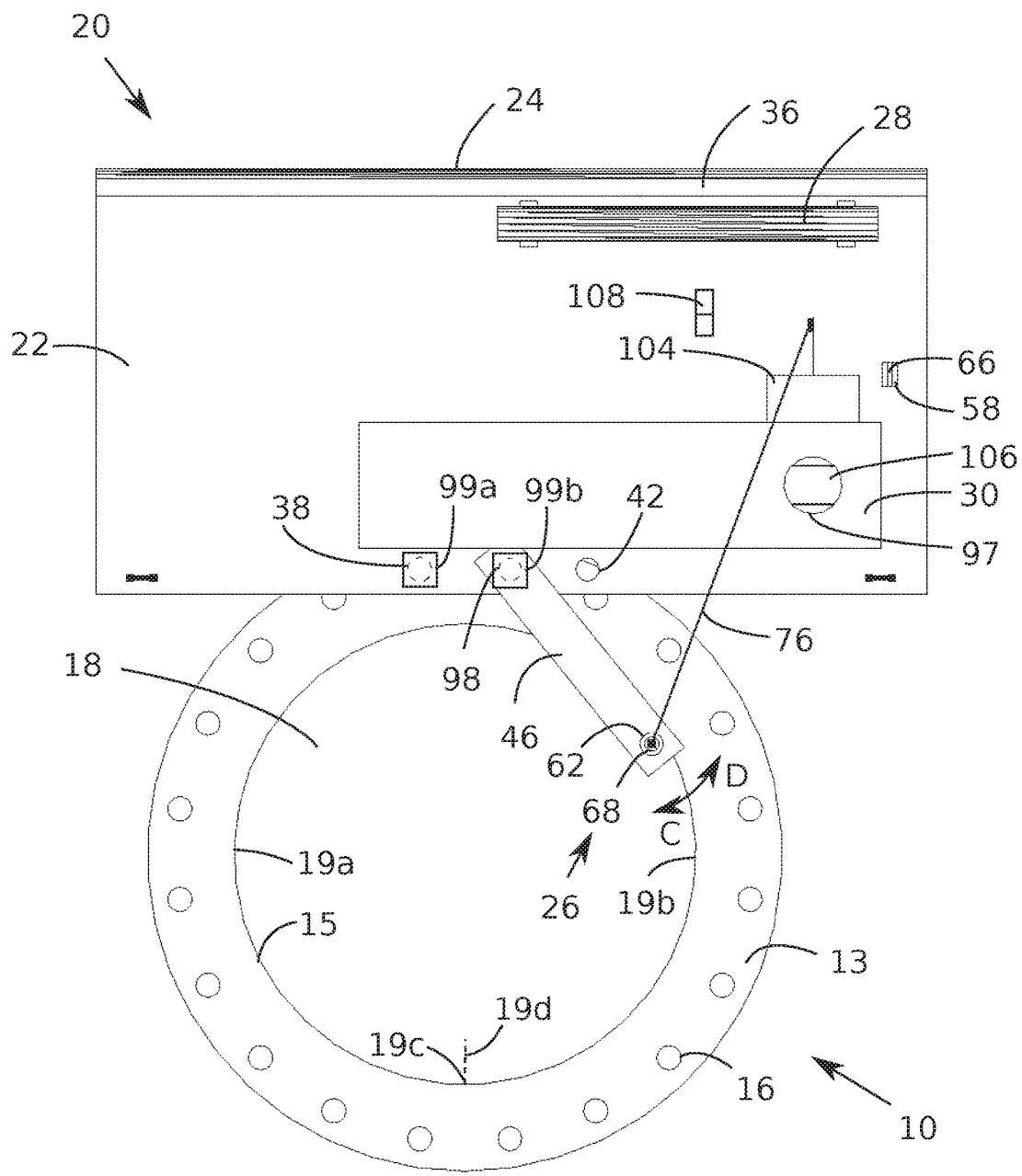
FIG. 2 is a front view of the confined space entry station and manway of FIG. 1.
Figure 3:
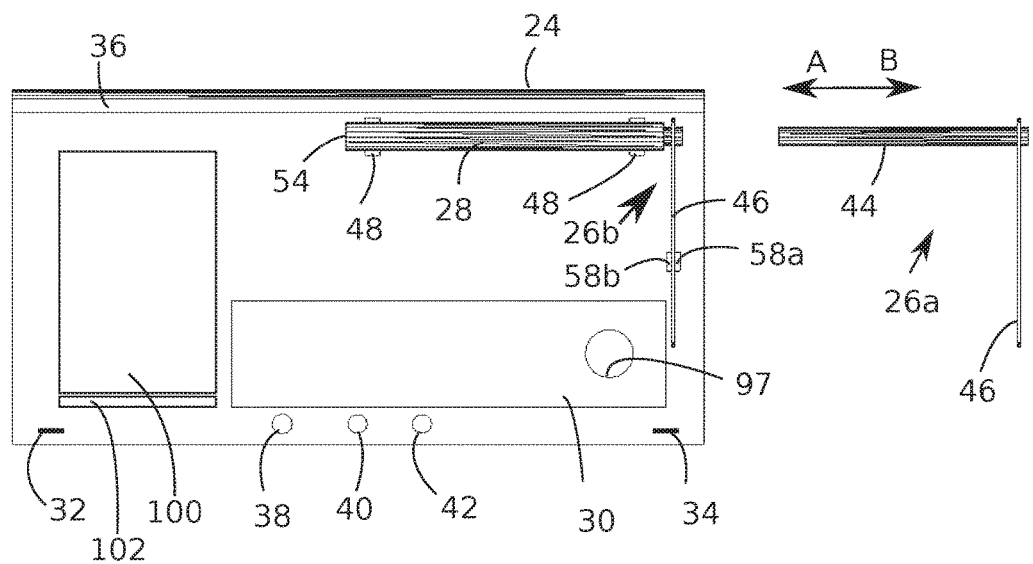
FIG. 3 is a front view of the confined space entry station of FIG. 1.

The probe arm 26 comprises a probe holding segment 44 and a connecting segment 46. The probe has a stored position where the probe holding segment is located within the probe arm support 28, as shown in FIG. 3, and a deployed position where the connecting segment 46 is attached adjacent a lower edge of the back plate 22, such as at apertures 38, 40 or 42, as shown in FIGS. 1 and 2.

The probe arm support 28 is attached to the back plate 22 by two spaced apart mounts 48. The probe arm support 28 comprises a receiving passage 50 along at least a portion of the elongated length of the probe arm support 28. The receiving passage 50 is sized to receive the probe holding segment 44 of the probe arm 26. In some embodiments, the probe holding segment 44 and the receiving passage 50 are cylindrical. In some embodiments, the receiving passage 50 extends from a receiving end 52 to an opposite end 54. In some embodiments, the receiving passage 50 extends from the receiving end 52, but stops short of the opposite end 54. While the probe arm support 28 is located in an upper right region of the back plate 22, it will be recognized that the probe arm support can be located at other locations on the back plate, such as an upper left region, a lower left region, a lower right region, or a central region. In some embodiments, the probe arm support 28, may be a flat surface, a curved surface such as a half circle, or other shapes capable of supporting the probe arm. Additional securing components such as a strap may be used to hold the probe arm to the probe arm support when the probe arm support does not enclose the probe holding segment 44.

In some embodiments, the probe arm support 28 and or the probe holding segment 44 are sized so that the probe holding segment 44 is friction fitted in the receiving passage 50. Therefore, the application by a user of a predetermined amount of force in the direction B of FIG. 3 is necessary to withdraw the probe holding segment 44 to overcome the friction fit. The friction fit prevents the unintended withdrawal of or falling out of the probe holding segment 44 from the probe arm support 28.

The back plate comprises a connecting segment engagement 58. The engagement comprises a block with a groove 66. The groove divides the block into two lateral blocking portions 58a, 58b. In some embodiments, the connecting segment 46 is frictionally gripped in the groove by the two lateral blocking portions of the engagement 58. The engagement 58 holds the connecting segment 46 on or adjacent the back plate 22 as shown in FIG. 3.

The probe arm 26 is shown in two alternate positions in FIG. 3. The probe arm 26 in position 26a of FIG. 3 is to the right of the probe arm support 28. The probe holding segment 44 is aligned with the receiving passage 50 of the probe arm support 28. The probe arm 26 is then moved from position 26a in the direction A to the position 26b where the probe holding segment 44 is received in the receiving passage 50. The probe holding segment 44 may be rotated so that the connecting segment 46 is received in the groove of the engagement 58. In FIG. 3, the connecting segment 46 is shown adjacent but spaced apart from the receiving end 52. In some embodiments, the probe arm 26 may be inserted into the receiving passage such that the connecting segment 46 is in surface-to-surface contact with the receiving end 52. The engagement 58 may be spaced so as to align the connecting segment 46 with surface to surface contact with the receiving end 52.

A probe end 60 of the connecting segment 46 comprises an aperture. The probe holding segment 44 comprises a recess. The probe holding segment 44 extends through the aperture at the recess. Therefore, a first portion 62 and a second portion 64 of the probe holding segment 44 are located on opposite sides of the connecting segment 46 at the aperture. The first portion 62 is shorter than the second portion 64.

The probe holding segment 44 comprises a hollow passage 68. In some embodiments, the passage 68 extends along the length of the probe holding segment from a first end 70 to a second end 72. Therefore the probe holding segment 44 has a hollow core extending through its length to allow a probe end 74 and probe tube 76 to pass through the probe holding segment 44. Each of the probe end and probe tube can be supported by the hollow passage 68.

Figure 5:
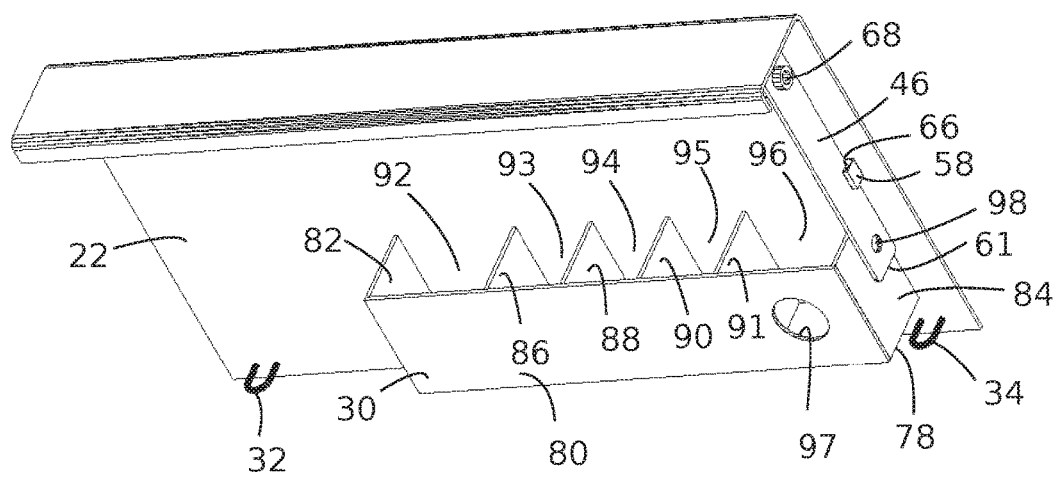
FIG. 5 is a front perspective view of the confined space entry station of FIG. 1.

As shown in FIG. 5, the accessory holder 30 comprises a bottom wall 78, a front wall 80, a left side wall 82, and a right side wall 84. In some embodiments, the accessory holder 30 comprises a plurality of internal walls 86, 88, 90, 91 dividing an interior of the accessory holder into a plurality of compartments 92, 93, 94, 95, 96. The front wall 80 may comprise one or more display apertures 97 providing front access to one or more compartments, such as compartment 96. The back plate 22 provides a rear wall to the accessory holder 30. In some embodiments, the accessory holder 30 comprised a top (not shown) that is hinged at the back wall to pivotally open to provide closable access to the internal space of the accessory holder. When the accessory holder does not comprise a top, the internal space is a semi-enclosed space having an open top.

In some embodiments, the engagement 58 is not used and instead the connecting segment 46 is releaseably attached to the right side wall 84 or otherwise to compartment 96. One or more apertures may be provided in the wall 84 and a wire or other fastener may extend from inside the compartment 96 around the connection segment 46 and back to the wall 84.

In some embodiments, accessory attachment members 32, 34 are U-shaped brackets attached to the back plate 22. Personal protective equipment, such as gloves, glasses, shields or other personal protective equipment can be attached and storied on the members 32, 34.

FIGS. 1 and 2 show the station 20 mounted to a manway or manhole 10. The manway comprises a first perimeter wall 11, a second perimeter wall 12, a front face 13, a back face 14, an interior wall 15, and a plurality of fastener apertures 16. The front face 13 is opposite the back face 14. The first and second perimeter walls 11, 12 are opposite the interior wall 15. The plurality of fastener aperture 16 are on a lip portion 17 of the front face 13. The lip portion 17 extends between the first perimeter wall 11 and the second perimeter wall 12. The interior wall 15 defines a perimeter boundary of the manway opening 18.

The manway 10 provides an entrance to a confined space, such as a tank, vessel, trenches, dike, liquid system, gas system, or the like. The object which the manway provides an entry to is not shown in FIGS. 1 and 2. However, such an object would extend from a first perimeter wall 11 and/or a second perimeter 12 wall of the manway 10. The manway 10 would provide access to the confined space via the manway opening 18. The manway 10 shown in FIGS. 1 and 2 is an exemplary manway, however the station 20 can be used on or adjacent any manway, manhole, or other access opening to a confined space. In some applications, the back plate 22 is not mounted to a manway, but is instead mounted to another stud or aperture or location adjacent to or in the vicinity of the manway or entry to a confined space. In some applications, the back plate is mounted to a portable device, such as a ladder, and the ladder is located adjacent to the entry to a confined space. In some applications, the ladder is an A-frame ladder.

In some embodiments, one or more alternate or additional mounting apertures are provided in other places on the back plate, other than the locations of apertures 38, 40, 42. In some embodiments, the one or more alternate or additional mounting apertures are located on the back plate between 1 inch and 3 inches, inclusive, below the top ledge 24 or the top edge of the back plate. In some embodiments, one or more alternate or additional mounting apertures are aligned the horizontal extent of probe arm support 28. The one or more alternate or additional mounting apertures are for mounting the back plate to a manway or other structure or device adjacent to the entry to a confined space In one application, such as shown in FIGS. 1 and 2, the back plate 22 is mounted to the front face 13 of the manway 10 at the top two of the fastener apertures 16. The first and second mounting apertures 38 and 40 are aligned with the top two of the fastener apertures 16 and fasteners 99a, 99b, such as bolts, secure the back plate 22 to the manway 10. In some embodiments, mounting studs extend through each of the fastener apertures 16 from the object or vessel to which the manway 10 is attached. When mounting studs are provided through one or more of the fastener apertures 16, the mounting apertures 38, 40 can receive those mounting studs and the fasteners 99a, 99b are nuts and are threaded onto the mounting studs to secure the back plate 22 against the front face 13 of the manway.

The figures show that the back plate comprises three mounting apertures 38, 40, 42. As is shown in FIGS. 1 and 2, not all mounting apertures need to be used to connect the back plate to the manway. Mounting aperture 42 is not aligned with a fastener aperture 16 of manway 10. The mounting apertures may be spaced equal distantly apart from each other, or may be spaced in a non-equidistant fashion. The mounting apertures may be spaced so that at least two mounting apertures can aligned with any of the various standard spacing provided between manway fastener apertures. In some embodiments, only two mounting apertures are provided in the back plate. In some embodiments, more than three mounting apertures are provided.

A user places the probe arm 26 into the deployed position by aligning a probe arm mounting aperture 98 with one of the mounting apertures 38, 40, 42 and ultimately with a manway fastener aperture 16 so that the probe arm can be mounted together with the back plate by a fastener and secured in position. The fastener or mounting stud may pass through the probe arm mounting aperture 98, the mounting aperture 40, and the fastener aperture 16.

The probe arm 26 is positionable by the user so that it is substantially out-of-the-way of most of the manway opening 18. In some applications, a user must crawl in the manway. Therefore the probe arm can be positioned adjacent the interior wall 15 in an area of the interior wall 15 above half-circle points 19a, 19b. In this manner, a user may crawl and occupy the space below the half-circle points 19a, 19b without hitting or stepping on the probe arm. The half-circle points 19a, 19b are each ninety degrees from a lower center point 19c where a vertical line 19d passing through the center of the circle of the manway opening meets the interior wall 15 at the bottom.

In some embodiments, the probe arm 26 is positionable adjacent the interior wall 15 at any point between 90 degrees and 180 degrees from the lower center point 19c in either direction. Therefore, the probe arm 26 may be positioned adjacent the interior wall 15 on the left side as compared to the right side shown in FIG. 2. Further, the probe arm 26 may be positioned at the top center adjacent the interior wall when the probe holding segment 44 has a length that is shorter than that shown in FIG. 2.

While the manway 10 is shown as a circle in FIGS. 1 and 2, it will be appreciated that the station 20 may be used at other manways of other shapes such as curved, oval, or quadrilateral.

In some embodiments, the probe arm 26 is not fastened to the back plate at a mounting aperture 38, 40, 42 but instead is removably fastened to the back plate adjacent to the bottom edge and or adjacent to the mounting apertures 38, 40, 42. In this way, the mounting of the back plate 22 to the manway is independent of the mounting of the probe arm 26 to the back plate 22.

The probe arm 26 is pivotal about its connection to the back plate in directions C and D of FIG. 2. The fastener used to fasten the probe arm to the back plate can be loosened or tightened to allow greater, lesser, or no pivotal movement of the probe arm 26 relative to the back plate.

As shown in FIG. 3, in some embodiments, the station 20 comprises a document holder 100. In some embodiments, the document holder 100 is a clipboard. In some embodiments, the document holder 100 is a plastic sleeve. In some applications, work-related papers, such as work permits, can be held by the document holder 100.

In some embodiments, the station 20 comprises a support ledge 102. The support ledge extends forward from the back plate 22. The support ledge 102 can support the document holder 100, documents, or it can support electronic devices capable of displaying electronic documents, such as an electronic tablet or other portable electronic device.

A portable gas vapor analyzer or monitor 104 can be placed in the accessory holder 30. FIGS. 1 and 2 show the monitor 104 in compartment 96 of the accessory holder 30. A display screen 106 of the monitor 104 is visible through the display aperture 97 of compartment 96, as shown in FIG. 2.

The monitor 104 can be any gas analyzer or monitor known in the art. One type of monitor 104 comprises a pump mechanism. The pump mechanism is coupled via a tube 76. In operation, a pump creates a suction within the tube. The probe end 74 is placed in the area where gas detection is desired to draw in and collect an air sample from that area, such as the area in the confined space adjacent to the manway. The pump draws the gas sample into the housing of the monitor 104.

The monitor 104 may use the following devices and/or procedures to analyze the gas sample and detect or measure a concentration of one or more elements or compound that may exist within the gas sample: a flame ionization detector, a catalytic bead sensor, an infrared detector, or other components or methods known in the art for detecting vapors or gases. The monitor can be configured to detect one or more of the following: oxygen, hydrogen sulfide, carbon monoxide, methane, ethane, ketone, propane, ethylene, butane, pentane, propylene, hexane, trimethylamine, heptane, hydrogen, nonane, methanol, ammonia, hydrogen, liquefied petroleum gas, and other combustible vapors and gases or other vapors and gases that could cause a risk to human health.

The monitor may comprises a internal electronic memory, a processor, an input device such buttons or a touch screen, an output device, such as an display screen to display the results of the analysis/detection, and a speaker for alerting the user to a detection of gases or vapors in excess of pre-defined or user-defined limits.

Figure 4:
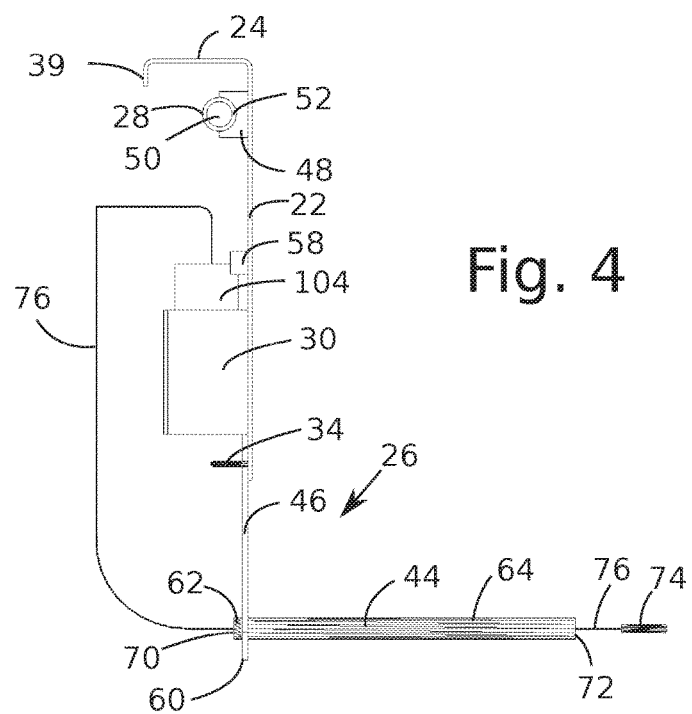
FIG. 4 is a right side view of the confined space entry station of FIG. 1.

When the monitor 104 is placed in the accessory holder 30, the tube 76 is then routed to and inserted in the first end 70 of the passage 68 of the probe holding segment 44. The tube 76 is pushed through the passage 68 and either stopped adjacent to the second end 72 or is pushed out beyond the second and an out of the probe holding segment 44 as shown in FIG. 4. The probe holding segment 44 extend through the manway and into the confined space adjacent the manway as shown in FIG. 1.

In some embodiments, the probe end 74 is not provided. Instead, a suction from the pump of the monitor draws air in a distal end of opening of probe tube 76. In some applications, a portion of the probe tube that extends through the probe holding segment 44 is rigid and a portion of the probe tube extending between the monitor 104 and the probe holding segment is flexible.

In some embodiments, as shown only in FIG. 2, the back plate comprises a tube or cable securing device 108, such as a strap, for securing excess probe tubing or cabling to the back plate 22 adjacent the accessory holder 30. The trap comprises two ends. Each end comprises fasteners, such as snaps fasteners or hook and loop fasteners, to allow the strap to be releasably closed about a coil of cabling or tubing.

In some applications, a two-way hand held radio (not shown) and an air horn or other sound generating warning device (not shown) may each be stored in compartments of the accessory holder 30.

Figure 6:
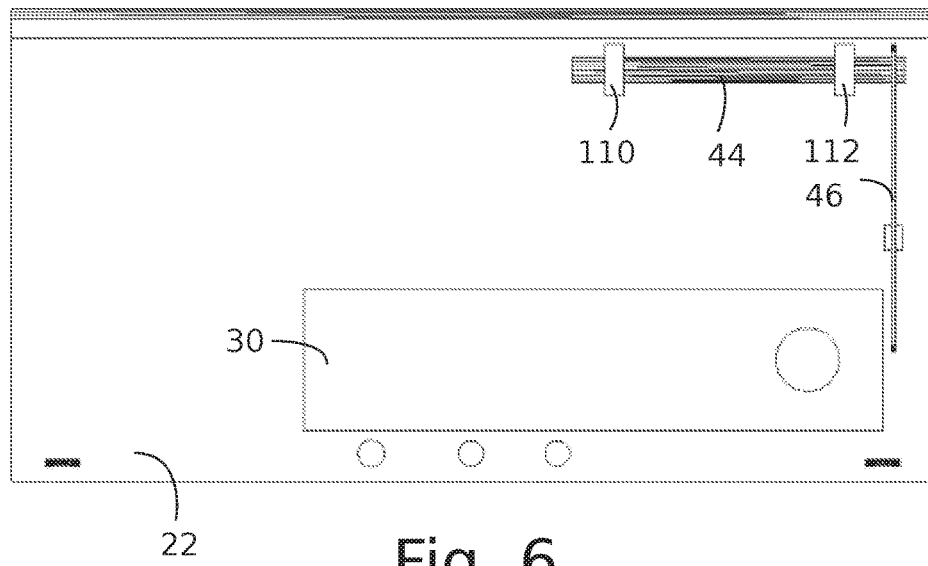
FIG. 6 is a front view of the station of FIG. 1 with second embodiment probe supports.
Figure 7:
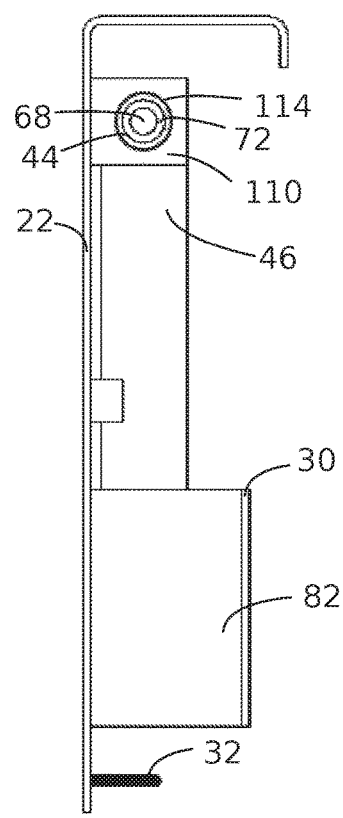
FIG. 7 a left side view of the station of FIG. 6.

FIGS. 6 and 7 show the station 20 with a second embodiment probe supports 110, 112 used in place of probe support 28 and mounts 48. The second embodiment probe supports are a first support block 110 and a second support block 112. Each of the support blocks 110, 112 are attached to the back plate 22 at spaced apart locations, such as shown in FIG. 6. The first and second support blocks are identical. Each support block comprise a through-going aperture 114 (not shown for block 112). The through-going aperture of each block is axially aligned with the through-going aperture of the other block. The apertures 114 of the blocks 110, 112 are sized to receive the probe holding segment 44 of the probe arm 26. Therefore the probe holding segment 44 can be inserted, retained, and removed in the blocks 110, 112 in the same manner as described with probe support 28.

In some embodiments, the apertures 114 of the blocks 110, 112 and or the probe holding segment 44 are sized so that the probe holding segment 44 is friction fitted in apertures 114. Therefore, the application by a user of a predetermined amount of force is necessary to withdraw the probe holding segment 44 to overcome the friction fit. The friction fit prevents the unintended withdrawal of or falling out of the probe holding segment 44 from the blocks 110, 112.

In one application, the use monitors the confined space for hazardous gases. The back plate 22 is mounted to a manway, such as at the apertures 16. The back plate may extend above the manway opening. If the probe arm 26, when deployed, is pivoted about its connection to the back plate to locate the probe arm adjacent to an internal sidewall 15 of the manway 10 in an upper half of the manway opening 18. The gas monitor 140 mounted to the back plate is activated to draw air through a probe tube 76 supported by the probe arm 26 extending through the manway opening 18 and into the confined space.

From the foregoing, it will be observed that numerous variations and modifications may be effected without departing from the spirit and scope of the invention. It is to be understood that no limitation with respect to the specific apparatus illustrated herein is intended or should be inferred.

The invention claimed is:

1. A confined space entry station, comprising:
a back plate configured to removably attach to a manway of a confined space;
an accessory holder connected to the back plate;
a probe holding arm comprising a connecting segment and a probe holding segment, the probe holding arm comprises a deployed position and a stored position, the connecting segment is connected to the probe holding segment, the probe holding segment is transverse to the connecting segment;
the connecting segment is pivotally connected to the back plate and extends beyond the back plate when the probe holding arm is in the deployed position; and,
the probe holding segment comprises a surface for supporting a probe, the probe holding segment extends transverse to the back plate when the probe holding arm is in the deployed position.

2. The station of claim 1, wherein the probe holding segment comprises a through passage, the through passage extends from a first end of the probe holding segment to a second end of the probe holding segment, the through passage comprises the surface for supporting the probe.

3. The station of claim 1, wherein the accessory holder is a gas monitor holder, the gas monitor holder comprises a front wall, and the front wall comprises a display opening.

4. The station of claim 1, wherein the connecting segment extends below the back plate when in the deployed position.

5. The station of claim 1, wherein the probe holding segment is perpendicular to the connecting segment.

6. The station of claim 1, the connecting segment is removably attached to the back plate, the back plate comprises a probe holding arm support, the probe holding segment is within an area of the back plate and is supported by the probe holding arm support when the probe holding arm is in the stored position.

7. The station of claim 6, wherein the probe holding arm support comprises a cylindrical receiving passage, and the probe holding segment comprises a cylindrical perimeter wall that is sized to fit into the cylindrical receiving passage.

8. The station of claim 7, wherein the cylindrical perimeter wall is sized to friction fit into the cylindrical receiving passage.

9. The station of claim 6, wherein the back plate comprises a support grip, the support grip comprises a groove, the support grip is configured to frictionally grip the connecting segment of the probe holding arm when the connecting segment is received in the groove and the probe holding arm is in the stored position.

10. The station of claim 6, wherein the probe holding arm support comprises a plurality of support blocks, each support block comprising a through-going aperture sized to receive the probe holding segment, each of the through-going apertures of the plurality of support blocks are axially aligned.

11. The station of claim 1, comprising a top ledge, the top ledge is connected to the back plate at an upper portion of the back plate, the top ledge extends forward from the back plate.

12. The station of claim 1, comprising a document holder attached to the back plate adjacent the accessory holder; and a U-shaped loop extending from the back plate.

13. The station of claim 1, the back plate comprises a plurality of mounting apertures located adjacent to a bottom edge of the back plate, the plurality of mounting apertures for connecting the back plate to the manway.

14. The station of claim 1, wherein
the probe holding segment comprises a through passage, the through passage extends from a first end of the probe holding segment to a second end of the probe holding segment, the through passage comprises the surface for supporting the probe;
the accessory holder is a gas monitor holder;
the connecting segment extends below the back plate when the connecting segment is in the deployed position;
the connecting segment is removably attached to the back plate, the back plate comprises a probe holding arm support, the probe holding segment is within an area of the back plate and is supported by the probe holding arm support when the probe holding arm is in the stored position; and,
the probe holding arm support comprises a cylindrical receiving passage, and the probe holding segment comprises a cylindrical perimeter wall that is sized to fit into the cylindrical receiving passage.

15. A gas monitor mount for a manway entrance to a confined space, comprising:
a back plate configured to removably attach to the manway of the confined space;
a gas monitor holder connected to the back plate;
a probe holding arm comprising a connecting segment and a probe holding segment, the probe holding arm comprises a deployed position and a stored position, the connecting segment is connected to the probe holding segment, the probe holding segment is transverse to the connecting segment;
the connecting segment is pivotally connected to the back plate and extends beyond the back plate when the probe holding arm is in the deployed position; and,
the probe holding segment comprises a surface for supporting a probe, the probe holding segment extends transverse to the back plate when the probe holding arm is in the deployed position.

16. The mount of claim 15, wherein gas monitor holder comprises a front wall, the front wall comprises a display opening.

17. The mount of claim 15, wherein the back plate comprises a plurality of mounting apertures for connecting the back plate to the manway.

18. The mount of claim 15, wherein the connecting segment is removably attached to the back plate, the back plate comprises a probe holding arm support, the probe holding segment is within an area of the back plate and is supported by the probe holding arm support when the probe holding arm is in the stored position.

19. The mount of claim 15, wherein
the probe holding segment comprises a through passage, the through passage extends from a first end of the probe holding segment to a second end of the probe holding segment, the through passage comprises the surface for supporting the probe;
the connecting segment extends below the back plate when the connecting segment is in the deployed position;
the connecting segment is removably attached to the back plate, the back plate comprises a probe holding arm support, the probe holding segment is within an area of the back plate and is supported by the probe holding arm support when the probe holding arm is in the stored position; and,
the probe holding arm support comprises a cylindrical receiving passage, and the probe holding segment comprises a cylindrical perimeter wall that is sized to fit into the cylindrical receiving passage.

20. A method of monitoring a confined space for hazardous gas, comprising the steps of:
attaching a back plate of a gas monitor mount at one or more apertures of a manway opening,
pivoting a probe holding arm, about a probe holding arm connection to the back plate, to locate the probe holding arm adjacent to an internal sidewall of the manway in an upper half of the manway opening; and,
activating a gas monitor mounted to the back plate to draw air through a tubular probe supported by the probe holding arm extending through the manway opening and into the confined space.

* * * * *